United States Patent
Watanabe et al.

(10) Patent No.: US 12,417,655 B2
(45) Date of Patent: Sep. 16, 2025

(54) EMOTION DETERMINATION SYSTEM AND METHOD FOR DETERMINING EMOTION

(71) Applicant: Anicom Holdings, Inc., Tokyo (JP)

(72) Inventors: Takuro Watanabe, Tokyo (JP); Mai Sato, Tokyo (JP); Tsuguna Inagaki, Tokyo (JP); Satoru Kurihara, Tokyo (JP); Mai Tsukada, Tokyo (JP); Natsumi Shinoda, Tokyo (JP); Naoyuki Takada, Tokyo (JP); Ayumi Kamijima, Tokyo (JP); Ayaka Tominaga, Tokyo (JP); Yuri Inui, Tokyo (JP); Nao Konno, Tokyo (JP); Megumi Kaneko, Tokyo (JP); Yusuke Iida, Tokyo (JP); Cheolhwan Choi, Tokyo (JP)

(73) Assignee: ANICOM HOLDINGS, INC., Tokyo (JP)

( * ) Notice: Subject to any disclaimer, the term of this patent is extended or adjusted under 35 U.S.C. 154(b) by 0 days.

(21) Appl. No.: 18/723,037

(22) PCT Filed: Dec. 22, 2022

(86) PCT No.: PCT/JP2022/047482
§ 371 (c)(1),
(2) Date: Sep. 19, 2024

(87) PCT Pub. No.: WO2023/120675
PCT Pub. Date: Jun. 29, 2023

(65) Prior Publication Data
US 2025/0111698 A1    Apr. 3, 2025

(30) Foreign Application Priority Data
Dec. 23, 2021  (JP) .................. 2021-209899

(51) Int. Cl.
*G06V 40/20*    (2022.01)
*G06V 10/764*   (2022.01)
*G06V 40/10*    (2022.01)

(52) U.S. Cl.
CPC ............ *G06V 40/20* (2022.01); *G06V 10/764* (2022.01); *G06V 40/10* (2022.01)

(58) Field of Classification Search
CPC ....... G06V 40/20; G06V 10/764; G06V 40/10
See application file for complete search history.

(56) References Cited

U.S. PATENT DOCUMENTS 11,216,643 B1 *   1/2022   Madden ................. G08B 25/10
12,171,196 B2 *  12/2024   Lonkar .................. G06V 40/10
(Continued)

FOREIGN PATENT DOCUMENTS

| CN | 111597942 A | 8/2020 |
| JP | 2000-76421 A | 3/2000 |

(Continued)

OTHER PUBLICATIONS

Decision of Refusal for Japanese Application No. 2021-209899, dated Mar. 29, 2023.
(Continued)

*Primary Examiner* — Santiago Garcia
(74) *Attorney, Agent, or Firm* — Birch, Stewart, Kolasch & Birch, LLP (57) ABSTRACT

The objective is to provide an emotion determination system and the like for determining the emotion of an animal by a simple method. The emotion determination system comprises: an acquisition unit for acquiring an image of an animal; a behavior information generation unit for generating behavior information relating to a behavior of the animal from the image of the animal acquired by the acquisition unit; and an emotion determination unit for determining the (Continued)

emotion of the animal based on the behavior information generated by the behavior information generation unit.

18 Claims, 7 Drawing Sheets

(56) References Cited

U.S. PATENT DOCUMENTS

| | | | |
|---|---|---|---|
| 2015/0099946 A1* | 4/2015 | Sahin | A61B 7/04 600/301 |
| 2015/0163412 A1* | 6/2015 | Holley | G08B 25/008 348/143 |
| 2018/0014512 A1* | 1/2018 | Arabani | A01K 29/005 |
| 2018/0054399 A1* | 2/2018 | Shinoda | H04L 51/02 |
| 2019/0037800 A1* | 2/2019 | Betts-Lacroix | A01K 29/005 |
| 2020/0202511 A1* | 6/2020 | Robertson | G06N 20/00 |
| 2020/0315141 A1 | 10/2020 | Kusui et al. | |
| 2021/0001077 A1* | 1/2021 | Stevens | B25J 13/08 |
| 2021/0089945 A1* | 3/2021 | Gibbs | G06N 5/02 |
| 2022/0000404 A1* | 1/2022 | Kim | A61B 5/165 |
| 2022/0114557 A1* | 4/2022 | Wang | G06V 20/10 |
| 2022/0281117 A1* | 9/2022 | Eskandari | A61B 5/0022 |
| 2023/0060020 A1* | 2/2023 | Lonkar | A01K 1/0082 |
| 2023/0070719 A1* | 3/2023 | Jeon | G06V 40/10 |
| 2023/0364423 A1* | 11/2023 | Lee | A61N 1/36082 |
| 2024/0296656 A1* | 9/2024 | Shevtsov | G06Q 30/0631 |

FOREIGN PATENT DOCUMENTS

| | | |
|---|---|---|
| JP | 2017-163947 A | 9/2017 |
| JP | 2018-166653 A | 11/2018 |
| JP | 2019-195295 A | 11/2019 |
| JP | 2020-5558 A | 1/2020 |
| JP | 2020-170916 A | 10/2020 |
| JP | 2021-125260 A | 8/2021 |
| JP | 2022-101295 A | 7/2022 |
| KR | 10-2019-0020513 A | 3/2019 |
| WO | WO 2016/125478 A1 | 8/2016 |
| WO | WO 2016/140332 A1 | 9/2016 |
| WO | WO 2022/138839 A1 | 6/2022 |

OTHER PUBLICATIONS

Decision to Grant a Patent for Japanese Application No. 2021-209899, dated Jul. 21, 2023.
International Search Report, issued in PCT/JP2022/047482, PCT/ISA/210, dated Jan. 31, 2023.
Notice of Reasons for Refusal for Japanese Application No. 2021-209899, dated Oct. 17, 2022.
Written Opinion of the International Searching Authority, issued in PCT/JP2022/047482, PCT/ISA/237, dated Jan. 31, 2023.
Notice of Reasons for Refusal for Japanese Application No. 2021-209899, dated Jan. 10, 2023.
Corujo et al., "Emotion Recognition in Horses with Convolutional Neural Networks," Arxiv.org, Cornell University Library, 2021, pp. 1-14.
Sinnott et al., "Run or Pat: Using Deep Learning to Classify the Species Type and Emotion of Pets," 2021 IEEE Asia-Pacific Conference on Computer Science and Data Engineering, 2021, pp. 1-6.
Tsai et al., "Multiple Feature Dependency Detection for Deep Learning Technology --- Smart Pet Surveillance System Implementation," Electronics, vol. 9, No. 1387, 2020, pp. 1-16.

* cited by examiner

EMOTION DETERMINATION SYSTEM AND METHOD FOR DETERMINING EMOTION

TECHNICAL FIELD

The present invention relates to an emotion determination system and a method for determining an emotion, and in particular, to an emotion determination system and a method for determining an emotion that uses an image of an animal to provide a determination result relating to an emotion of the animal.

BACKGROUND ART

Pets, such as dogs, cats, and rabbits, are irreplaceable companions to human beings, and various services for pets have been spreading and developing.

Animals kept as pets are individual creatures with their own personalities and emotions. Understanding the emotions of animals can make communication between pets and owners smoother and deeper, preventing misunderstandings and mismatches between pets and owners, and ultimately reducing the number of unfortunate cases such as pet abandonment.

However, animals cannot speak and, thus, cannot explain their emotions.

Patent Document 1 discloses an animal imaging device that takes an image of an animal while it defecates, and a health determination system that determines at least one of the health condition and emotion of the animal based on the image taken of the animal. However, determining an emotion based on an animal behavior is not disclosed.

Patent Document 2 discloses an information processing device comprising: a state determination unit for determining the state of an animal based on an image taken of the animal; an emotion determination unit for determining the emotion of the animal corresponding to the state of the animal determined by the state determination unit based on information indicating a relationship between the state of the animal and the emotion; and a notification processing unit for notifying a terminal of a message indicating the emotion of the animal as determined by the emotion determination unit. However, determining an emotion based on an animal behavior is not disclosed.

RELATED ART DOCUMENTS

Patent Documents

[Patent Document 1] JP2020-5558A
[Patent Document 2] JP2020-170916A

SUMMARY OF THE INVENTION

Problems to be Solved by the Invention

Thus, the objective of the present invention is to provide an emotion determination system and a method for determining an emotion of an animal by a simple method.

Means for Solving the Problems

As a result of diligent study to solve the above-mentioned problems, the Inventors have found that it is possible to analyze an image of an animal and determine or estimate the emotion of the animal from behavior information of the animal that represents what kind of behavior the animal is engaging in in the image, and have arrived at the present invention.

In other words, the present invention can be described as the following [1] to [13]:

[1] An emotion determination system comprising: an acquisition unit for acquiring an image of an animal; a behavior information generation unit for generating behavior information relating to a behavior of the animal from the image of the animal acquired by the acquisition unit; and an emotion determination unit for determining an emotion of the animal based on the behavior information generated by the behavior information generation unit.

[2] The emotion determination system according to [1], wherein the behavior information generation unit extracts a feature value from the image of the animal and generates behavior information by determining the behavior of the animal based on the feature value.

[3] The emotion determination system according [1], wherein the behavior information generation unit comprises a learned model that has learned a relationship between an image of an animal and a behavior of the animal, and generates behavior information by determining the behavior using the learned model.

[4] The emotion determination system according to any one of [1] to [3], wherein the behavior information generation unit generates behavior information for each behavior when a plurality of types of behaviors are included in the image.

[5] The emotion determination system according to any one of [1] to [4], wherein, when the behavior information generation unit generates behavior information, the behavior information is weighted according to a length of the duration of the behavior.

[6] The emotion determination system according to any one of [1] to [5], further comprising a database storing correspondence between behavior information and emotions, wherein the emotion determination unit determines an emotion of the animal by referring to the database.

[7] The emotion determination system according to any one of [1] to [6], further comprising a breed determination unit for determining a breed of the animal from the image of the animal acquired by the acquisition unit.

[8] The emotion determination system according to any one of [1] to [7], wherein the database is a database storing correspondence between behavior information and emotions for each species or breed.

[9] The emotion determination system according to any one of [1] to [7], further comprising: a plurality of the databases according to a classification that classifies a breed of an animal based on an average adult weight of the breed.

[10] A method for generating a learned model for determining a behavior of an animal from an image of the animal, wherein an image of an animal and a label relating to a behavior of the animal are input as teacher data to a computer in order to train an artificial intelligence.

[11] An emotion determination method comprising: a step of preparing an image of an animal: a behavior information generation step of generating behavior information relating to a behavior of the animal from the image of the animal by a computer; and an emotion determination step of determining an emotion of the animal based on the behavior information by a computer.

[12] The emotion determination method according to [11], wherein the behavior information generation step is a step of generating behavior information by extracting a feature value from the image of the animal and determining the behavior of the animal based on the feature value.

[13] The emotion determination method according to [12], wherein the behavior information generation step is a step of generating behavior information by determining the behavior using a learned model that has learned a relationship between an image of an animal and a behavior of the animal.

Effects of the Invention

The present invention makes it possible to provide an emotion determination system and an emotion determination method for determining an emotion of an animal by a simple method.

MODE FOR CARRYING OUT THE INVENTION

<Emotion Determination System>

The emotion determination system of an embodiment of the present invention comprises: an acquisition unit for acquiring an image of an animal: a behavior information generation unit for generating behavior information relating to a behavior of the animal from the image of the animal acquired by the acquisition unit; and an emotion determination unit for determining an emotion of the animal based on the behavior information generated by the behavior information generation unit. Note that the comprehensive or specific aspects thereof may be realized in a system, apparatus, method, integrated circuit, computer program, recording medium, or in any combination of a system, apparatus, method, integrated circuit, computer program, and recording medium.

[Acquisition Unit]

The acquisition unit acquires an image of an animal. Unless otherwise specified, an "image" includes both a still image and a video. The acquisition unit may be configured to accept an image transmitted and/or input from an external terminal or a computer, or may be a camera equipped with a lens and an image sensor. The target animals include mammals such as dogs, cats, and rabbits: dogs and cats are preferred. The method of accepting an image may be any of scanning, inputting or transmitting image data, or capturing an image by taking the image on the spot. The format of the image is not limited and can be either a still image or a moving image. However, an emotion can be determined more accurately with a moving image since a plurality of still images can be acquired from a moving image. Although the parts of the animal in the image are not particularly limited, an image of an animal that is easy to determine what kind of behavior the animal is engaged in, for example, an image that includes the face (especially the eyes and ears), tail, and other parts of the animal that easily exhibits an emotion, or an image that includes the whole body, are preferred. The image may be black and white, grayscale, or color. An image whose shape has been edited using image editing software, an image containing a plurality of animals, and an image in which the eyes or ears are too small to be distinguished or blurred, are not desirable. The image may be normalized or have a uniform resolution.

[Behavior Information Generation Unit].

The behavior information generation unit generates behavior information relating to a behavior of an animal from an image of the animal acquired by the acquisition unit. For example, the behavior information generation unit analyzes image data to determine a behavior classification of a pet. The behavior information generation unit preferably generates behavior information by extracting a feature value from an image of an animal and determining the behavior of the animal based on the feature value. It is also preferable that the behavior information generation unit has a learned model that has learned a relationship between an image of an animal and a behavior of the animal, and generates behavior information by determining a behavior by the learned model.

Behavior information is information, a tag, and/or the like about a behavior. For example, it is information about a behavior classification. In the case of dogs, behavior classifications include one or more of the behaviors selected from, for example, wagging tail, slumping down tail, curling tail, tucking tail between legs, jumping, circling, barking, growling, sniffing, licking nose, yawning, scratching body, shaking, looking away, sniffing smell, lifting one paw, nuzzling someone's leg, licking, chewing, running, lying down, turning over and showing the belly, sitting, perking up ears, putting ears back, opening mouth, digging a hole, and panting. In the case of cats, behavior classifications include one or more of the behaviors selected from, for example, rounding pupils, sharpening eyes, squinting, pointing ears forward, pointing ears back, opening mouth wide with fangs bared, pursing month, flaccid whiskers, pointing whiskers upward, positioning head below shoulders, rubbing head against something, bristling head fur, lying down with belly showing, rubbing body against an owner, rubbing body against a wall, lowering front trunk and raising hindquarters, gripping the ground with claws out, tensing limbs and lifting back, raising tail, bristling tail fur, curling tail, slapping tail, and slumping down tail. These are examples only, and other behaviors may be used as behavior information. Alternatively, not all of these examples may be classified as behavior information, and only behaviors with strong connection to emotion may be classified as behavior information. Behavior information can also be information such as a tag, number, or symbol assigned to each behavior.

When the behavior information generation unit comprises a learned model, the learned model can be generated, for example, by supervised learning or unsupervised learning. In the case of supervised learning, the teacher data can be, for example, an image of an animal and data or a label related to a behavior of the animal. An image of an animal that is tagged or labeled according to the behavior of the animal may also be used as teacher data.

The format of the animal image used as teacher data is not limited. It can be a still image or a moving image. Although the parts of the animal in the image are not particularly limited, an image of an animal that is easy to determine the behavior of the animal, for example, an image that includes the face and tail, or an image that includes the whole body, are preferred. The image may be black and white, grayscale, or color. An image whose shape has been edited using image editing software, an image containing a plurality of animals, and an image in which the eyes or ears are too small to be distinguished or blurred, are not desirable. The image may preferably be normalized or have a uniform resolution. The resolutions of the image used as the teacher data and the image accepted by the acquisition unit are preferably unified.

The behavior of the animal in an image used as teacher data can be identified from the video. Other methods for identifying a behavior than using a video include identifying a behavior based on, for example, a questionnaire to a pet owner or descriptions on a pet insurance application.

The learned model is preferably artificial intelligence (AI). Artificial intelligence (AI) refers to software or a system that mimics the intellectual tasks performed by the human brain through a computer, specifically a computer program that understands natural language used by humans, performs logical reasoning, and learns from experience. Artificial intelligence may be general-purpose or specialized, and may be any of the known types, such as logistic regression, decision trees, k-means, multilayer perceptrons, recurrent neural network, deep neural network, convolutional neural network, or any other publicly available software can be used.

The artificial intelligence is trained to generate a learned model. Learning can be either machine learning or deep learning, but deep learning is preferred. Deep learning is an advanced form of machine learning and has a quality of ability to automatically find feature values.

The learning method for generating a learned model is not particularly limited and publicly available software or libraries can be used. The learning method may be transfer learning. For example, DIGITS (the Deep Learning GPU Training System) published by NVIDIA can be used. Also, for example, ResNet, MobileNet, or EfficientNet can be used as artificial intelligence (a neural network), and a machine learning library (a deep learning library) such as Pytorch can be used to generate a learned model by transfer learning. Other known support vector machines, for example, those disclosed in "An Introduction to Support Vector Machines and Other Kernel-based Learning Methods" (Kyoritsu Shuppan) may also be used.

When a plurality of types of behaviors are included in an image, it is preferable for the behavior information generation unit to generate behavior information for each of the behaviors. For example, if a dog wags its tail for 30 seconds and then raises one paw for 30 seconds in a one-minute video, "wagging tail" and "raising one paw" are generated as behavior information. If the dog simultaneously wags its tail and raises one paw during the video, the behavior information may be generated as a single action "wagging tail and raising one paw," or the behavior information may be generated separately for each action of "wagging tail" and "raising paw." Preferably, the behavior information is generated for each of the actions. When the behavior information generation unit generates the behavior information, it is preferable to weight each behavior information according to the length of the duration of the behavior, and if weighting is performed, information about the weighting should be generated along with each behavior information. For example, if a dog wags its tail for 70 seconds and then raises one paw for 30 seconds in a one-minute and 40-second video, "wagging tail" and "raising one paw" are generated as behavior information, and the weight of the "wagging tail" behavior is set to 0.7 and the "raising one paw" behavior is set to 0.3. If the tail hangs down for the entire duration of a one-minute video, "hanging down tail" is set to the behavior information, and the weight is set to 1.0. When weighing, it is preferable to multiply the weight by the emotion points assigned to each behavior information to make the final emotion determination. When a plurality of pieces of behavior information is generated, the emotion points for each behavior information are preferably added to make the emotion determination result.

[Emotion Determination Unit]

The emotion determination unit determines an emotion of an animal based on the behavior information generated by the behavior information generation unit. For example, specific behavior information is stored in advance in association with a specific emotion, and when the emotion determination unit receives the specific behavior information, it selects and determines the corresponding emotion. Determining an emotion may include, for example, predicting or estimating an emotion. It may also include determining which tendency each emotion item has, or assigning a score to each emotion. The determination may be a graded evaluation based on the strength of the tendency of each emotion item.

It is also preferable that the emotion determination system comprises a database storing correspondence between behavior information and emotions and that the emotion determination unit determines an emotion from behavior information by referring to the database. The database is preferably a database storing correspondence between behavior information and emotions for each species or breed. For example, a behavior and emotion database for dogs, a behavior and emotion database for cats, a behavior and emotion database for rabbits, and the like. Examples of the breed-specific database include a behavior and emotion database for Chihuahuas and a behavior and emotion database for Siberian Huskies. It is also preferred that a plurality of databases is provided according to classifications of animal breeds that are classified based on the average adult weights of the breeds. For example, databases for large dogs, medium dogs, small dogs, and miniature dogs may be respectively provided. For example, in the case of dogs, breeds of dogs can be classified by the average weights, such as, miniature dogs for breeds with an average adult (adult dog) weight of less than 4 kg, small dogs for breeds with an average weight of 4 kg to less than 10 kg, medium dogs for breeds with an average weight of 10 kg to less than 25 kg, and large dogs for breeds with an average weight of 25 kg or more. In addition, breeds may be classified by height, length, genetic relationship, and/or the like. Note that databases are not essential in the present invention. For example, if the emotion determination unit includes dictionary data on the relationship between behavior information and emotions, a separate database is not necessary.

The emotion determination unit may be configured to have a learned model that has learned the relationship between the types of animal behaviors and emotions and to determine an emotion from the behavior information using the learned model. The learned model can be generated, for example, by supervised learning or unsupervised learning. When a learned model is used, the database storing the relationship between behavior information and emotions may be unnecessary. In the case of supervised learning, the teacher data can be, for example, a behavior of an animal and data or a label related to the emotion of the animal. An image of an animal that is tagged or labeled according to the behavior and emotion of the animal may also be used as teacher data. Other configurations of the learned model are similar to those described with regard to the behavior information generation unit above.

[Breed Determination Unit]

Preferably, the emotion determination system of the present invention further includes a breed determination unit. The breed determination unit is a means to determine the breed of an animal from an image of the animal input to the above-mentioned acquisition unit using a learned model for determining the breed. Note that if the breed determination unit is not provided, the system can be configured to separately input breed information from a user terminal or the like.

In the case of humans, there is no reason to provide a breed determination unit because there is not much difference in the positions and shapes of key facial parts (for example, eyes, nose, and mouth). However, because pets have been repeatedly selectively bred by humans, behavior and emotional tendencies and the correspondence between behaviors and emotions may differ among different breeds. Therefore, the breed determination unit makes it possible to determine emotions more accurately.

The details of the images related to the breed determination unit are similar to those described with regard to the behavior information generation unit above.

The learned model for determining the breed is a learned model that has learned the relationship between an image of an animal and the breed of the animal. Preferably, the learned model is trained using an image of an animal and the breed of the animal as teacher data, to which an image of an animal is input and from which determination of the breed of the animal is output. The image of an animal as teacher data is similar to the one described with regard to the emotion determination unit above. The learned model for determining the breed is similar to the learned model in the emotion determination unit above, except that the learned model has learned the relationship between an image of an animal and the breed of the animal. The learned model may use a different algorithm, software, library, or learning method than the learned model in the above behavior information generation unit and emotion determination unit, or may use the same algorithm, software, library, or learning method as those used therein.

A breed is a unit of biological population below a species. For example, with regard to dogs, the types of dogs are also called dog breeds. Specifically, the dog breeds include Toy Poodle, Chihuahua, Miniature Dachshund, Shiba Inu, Pomeranian, Yorkshire Terrier, Miniature Schnauzer, Shih Tzu, French Bulldog, Papillon, Maltese, Labrador, Dalmatian, and Chow Chow. With regard to cats, the types of cats are also called cat breeds. Specifically, the cat breeds include Scottish Fold, American Shorthair, Norwegian Forest Cat, Russian Blue, British Shorthair, Ragdoll, Maine Coon, and Persian. With regard to rabbits, the rabbit breeds include the Netherland Dwarf, Holland Lop, Lop-Ear, Mini Rex, Dwarf Lop, and American Fuzzy Lop.

The emotion determination system of the present invention may comprise a plurality of learned models as the emotion determination unit and determine an emotion of an animal from an image of the animal input to the acquisition unit using the learned models corresponding to the result of determination of a breed by the breed determination unit or the information on a breed that was input at the same time when the image was received by the acquisition unit. When the emotion determination system of the present invention comprises the breed determination unit, it is preferable to determine the breed of an animal from an image of the animal input to the acquisition unit, and to determine the emotion using a corresponding learned model by the emotion determination unit based on the determination result of the breed and the behavior information.

The learned model corresponding to a breed is preferably one that has been learned using images of animals pertaining to one or more specific breeds and labels related to the emotions of the animals as teacher data. For example, the learned model is a learned model that has learned using images of animals that are a collection of only specific breeds and labels related to the emotions of the animals. In such a case, the images of animals that are a collection of only specific breeds may be images of only one breed, for example, Toy Poodle, or may be images of a plurality of breeds, for example, Toy poodle, Pomeranian, and Miniature dachshund. In the case of a plurality of breeds, breeds may be classified and a learned model may be configured for each classification, such as a learned model for large breeds trained using images of large breeds, a learned model for medium breeds trained using images of medium breeds, a learned model for small breeds trained using images of small breeds, and a learned model for miniature breeds trained using images of miniature breeds. Dogs also can be classified by the average weights: for example, miniature dogs for breeds with an average adult (adult dog) weight of less than 4 kg, small dogs for breeds with an average weight of 4 kg to less than 10 kg, medium dogs for breeds with an average weight of 10 kg to less than 25 kg, and large dogs for breeds with an average weight of 25 kg or more. In addition, breeds may be classified by height, length, genetic relationship, and/or the like.

[Output]

The emotion determination unit determines an emotion of an animal based on the behavior information of the animal. The format of the output of the determination result is not particularly limited. For example, texts or icons representing types of emotions can be displayed on the screen of a PC or mobile terminal used by the user, such as "happy," "relaxed," "seeking affection," "fun," "good mood," or "alerted." Alternatively, a plurality of emotion items are prepared and a tendency of each item is displayed as a score or a percentage. Specifically, 0.45 points for "happy," 0.35 points for "seeking affection", and/or the like (the higher the score, the stronger the emotion tends to be). The emotion determination system of the present invention may separately have an output unit that receives a determination result from the emotion determination unit and outputs the determination result and a transmission unit that transmits the determination result to a personal computer or mobile terminal used by the user through a communication line.

An embodiment of the emotion determination system of the present invention is described below with reference to FIG. 4.

Figure 1:
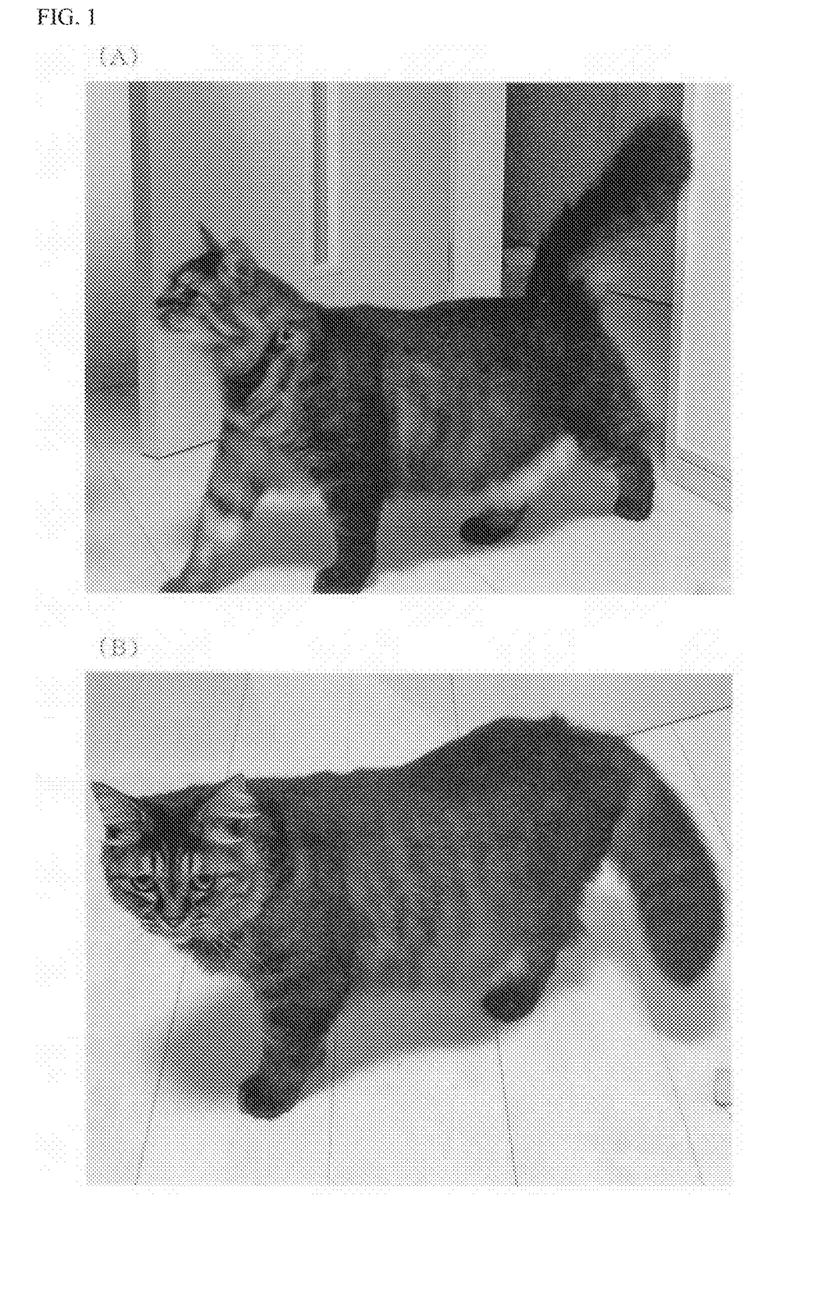
FIG. 1 is a diagram illustrating an exemplary image used as teacher data in an example.
Figure 2:
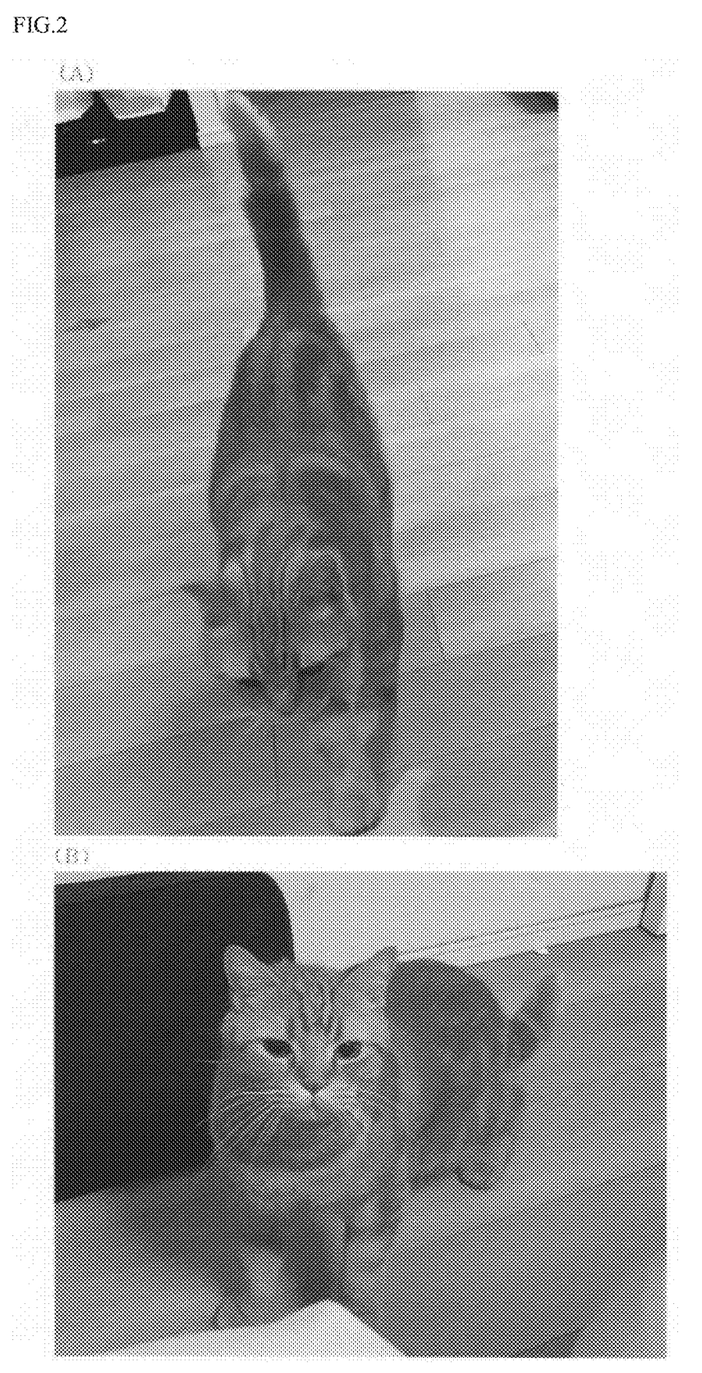
FIG. 2 is a diagram illustrating an exemplary image used as teacher data in an example.
Figure 3:
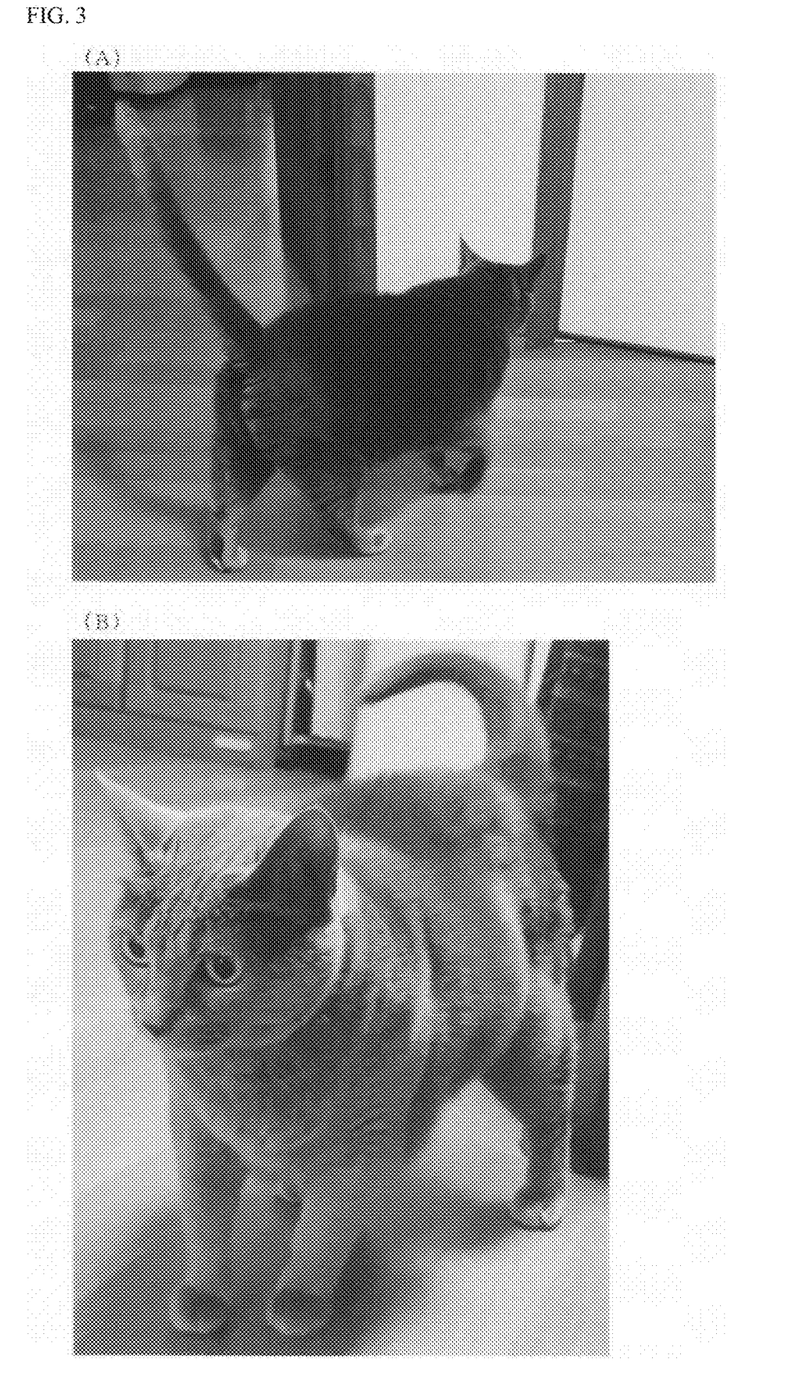
FIG. 3 is a diagram illustrating an exemplary image used as teacher data in an example.
Figure 4:
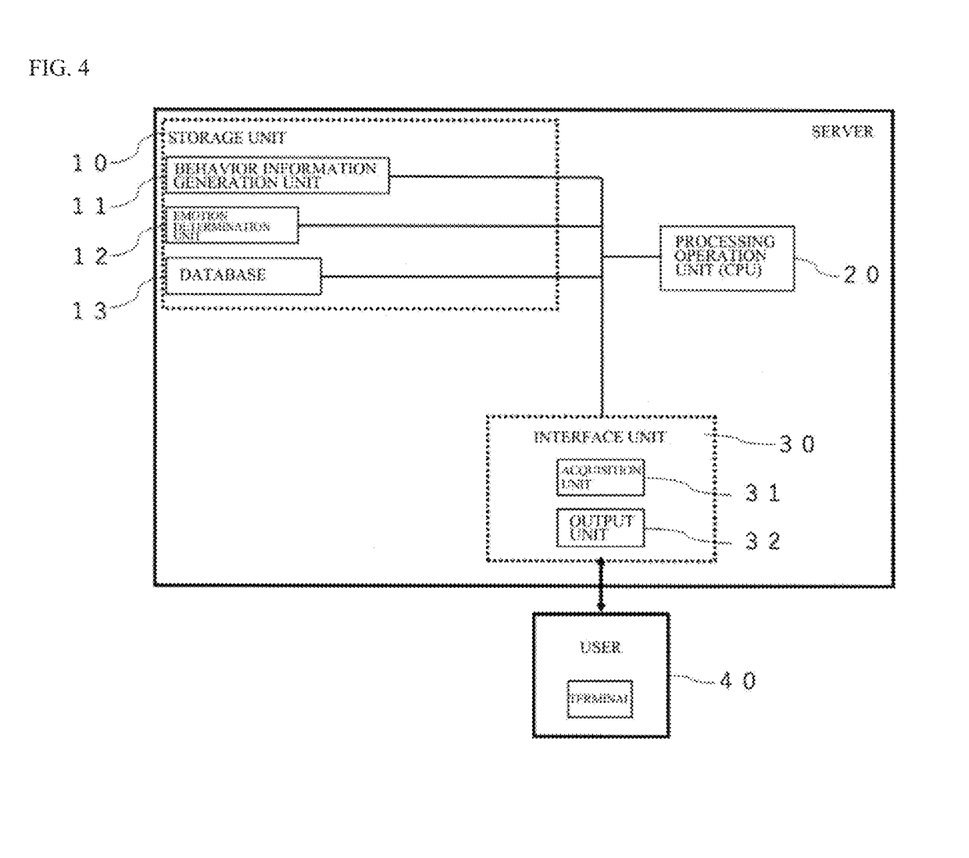
FIG. 4 is a schematic diagram illustrating an embodiment of the emotion determination system of the present invention.

In FIG. 4, a terminal 40 is a terminal used by a user. The user is, for example, a pet owner who wants to know the emotion of their pet. The terminal 40 is, for example, a portable information terminal such as a personal computer, smartphone, or tablet terminal. The terminal 40 comprises a processing unit such as a CPU, a storage unit such as a hard disk, ROM, or RAM, a display unit such as an LCD panel, an input unit such as a mouse, keyboard, or touch panel, and a communication unit such as a network adapter.

The user accesses the server from the terminal 40 and inputs and transmits an image (a photograph) of an animal and information such as the type, breed, sex, and weight of the animal. The user may take a picture or moving image of the target animal using the camera of a smartphone on the spot and then input and transmit the picture or moving image when using the emotion determination system. For example, the user follows an instruction displayed on the screen of the terminal 40 to take a moving image of the target animal and, when an appropriate moving image is taken, transmits it to the server through the Internet. At this time, the server may comprise a separate picture-taking auxiliary means comprising an image determination program, and the picture-taking auxiliary means may determine whether the moving image is suitable for determining an emotion, such as whether the moving image captured a behavior of the animal, and communicate the determination result to the user through the interface or terminal. The user can also receive the result of the emotion determination by the server by accessing the server through the terminal 40.

In the present embodiment, the server is configured by a computer, but the server may be any device as long as it has the functions of the present invention. The server may be a server on the cloud.

The storage unit 10 is configured by, for example, ROM, RAM, or a hard disk. The storage unit 10 stores an information processing program for operating each unit of the server, the behavior information generation unit 11, and the emotion determination unit 12.

The behavior information generation unit 11 analyzes an image of an animal obtained through input, transmission, or the like by the user, determines the behavior of the animal in the image, and generates animal behavior information. The emotion determination unit 12 determines the corresponding animal emotion from the animal behavior information. If a database 13 that stores the correspondence between animal behavior information and emotions exists, the emotion determination unit selects and determines the emotion from the behavior information by referring to the database 13. The behavior information generation unit 11 and the emotion determination unit 12 of the present embodiment may include, for example, a deep neural network or a convolutional neural network.

The processing operation unit 20 generates behavior information using the information processing program of the behavior information generation unit 11 stored in the storage unit. In addition, the processing operation unit 20 determines the emotion using the information processing program of the emotion determination unit stored in the storage unit.

The interface unit (the communication unit) 30 comprises the acquisition unit 31 and the output unit 32, accepts an image of an animal and other information, such as information on the species and breed of the animal, from the user terminal, and outputs and transmits the result of the emotion determination to the user terminal.

With the emotion determination system of the present embodiment, a user can easily obtain the determination result of the emotion of a pet by uploading a photograph, moving image, or the like of the pet to the server.

In the present embodiment, the behavior information generation unit, the emotion determination unit, and the acquisition unit are stored in the server that is connected to a terminal of a user through a connection means such as the Internet or LAN. However, the present invention is not limited to such a configuration, and the behavior information generation unit, emotion determination unit, database, and interface unit may be stored in a single server or device: each of them may be stored in a separate server; or the terminal used by a user may not be required.

Figure 5:
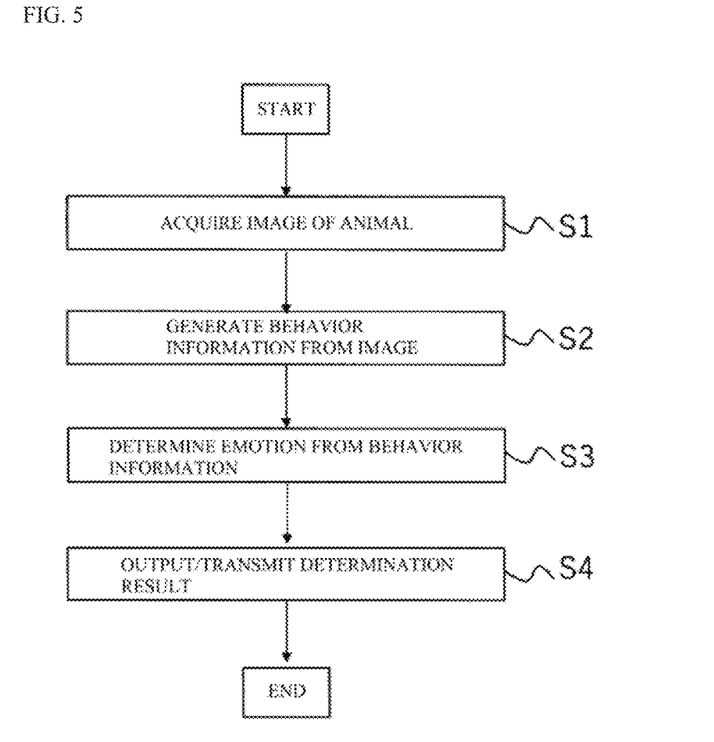
FIG. 5 is a flowchart diagram illustrating an example of the flow of emotion determination by the emotion determination system of the present invention.

FIG. 5 illustrates a flowchart of emotion determination according to an embodiment of the emotion determination system of the present invention. A user inputs basic information such as the species, breed, age, and sex of a target animal to the acquisition unit, and uploads an image of the animal (step S1). The processing operation unit of the server determines the behavior of the animal from the uploaded image using the behavior information generation unit (step S2). The emotion determination unit determines the emotion of the animal from the information generated by the behavior information generation unit (step S3), and the output unit outputs and presents the derived determination result to the user by displaying it on a screen or by other means (step S4).

<Embodiment with the Breed Determination Unit>

Figure 6:
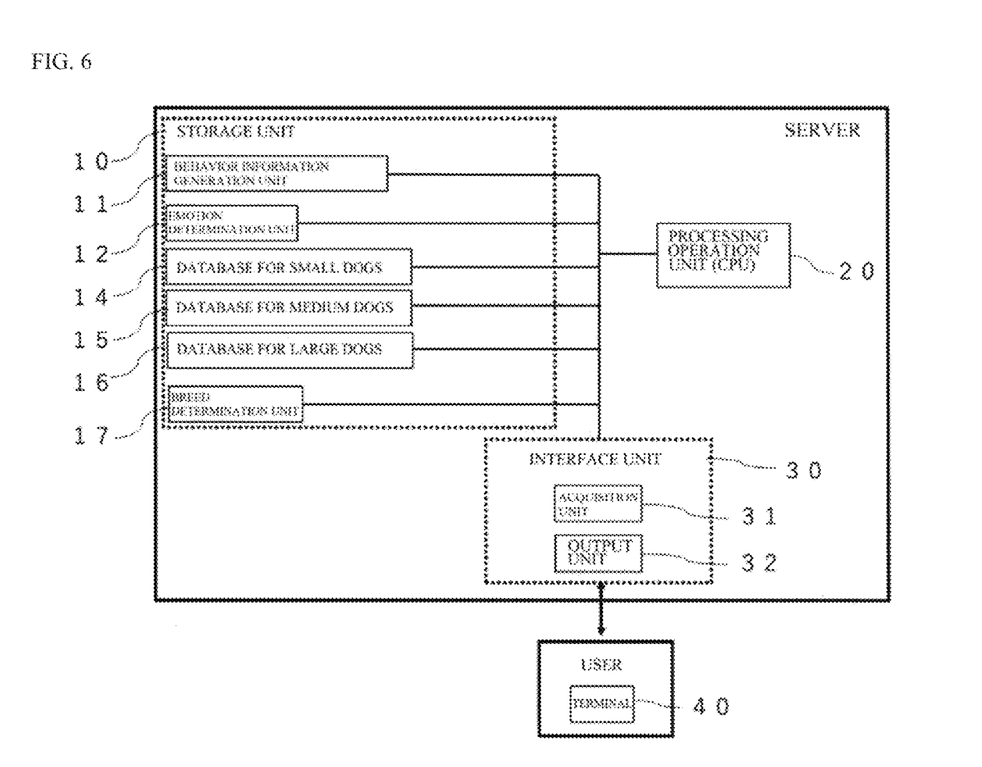
FIG. 6 is a schematic diagram illustrating an embodiment of the emotion determination system of the present invention (a case in which the breed is determined before the emotion is determined).

The following describes an embodiment of the emotion determination system comprising the breed determination unit with reference to FIG. 6.

The emotion determination system illustrated in FIG. 6 is similar to the above embodiment except that the storage unit 10 stores a database for small dogs 14, a database for medium dogs 15, a database for large dogs 16, and a breed determination unit 17, in addition to the behavior information generation unit 11 and the emotion determination unit 12.

In the emotion determination system according to the present embodiment, when an image of an animal is input to the acquisition unit 31, the breed determination unit 17 determines the breed of the animal. The determination of the breed may be determination of a specific breed name or determination regarding classifications, such as whether it is a large breed, a medium breed, or a small breed.

The database to be used for emotion determination is selected based on the determination result by the breed determination unit 17. A program or software may be provided to select the most suitable database from a plurality of databases according to the breed or the classification of breed. For example, if an image of an animal input to the acquisition unit is determined to be an image of a large breed, the database for large dogs 16 is selected and determination of the emotion is made from the behavior information.

Although the present embodiment assumes that a single emotion determination system is used for each species, for example, one for dogs and one for cats, the emotion determination system may be used for a plurality of species of animals. In such a case, it is preferable to have a species determination unit that determines the species of an animal from an image of the animal, and to have a plurality of databases for each species and breed.

Figure 7:
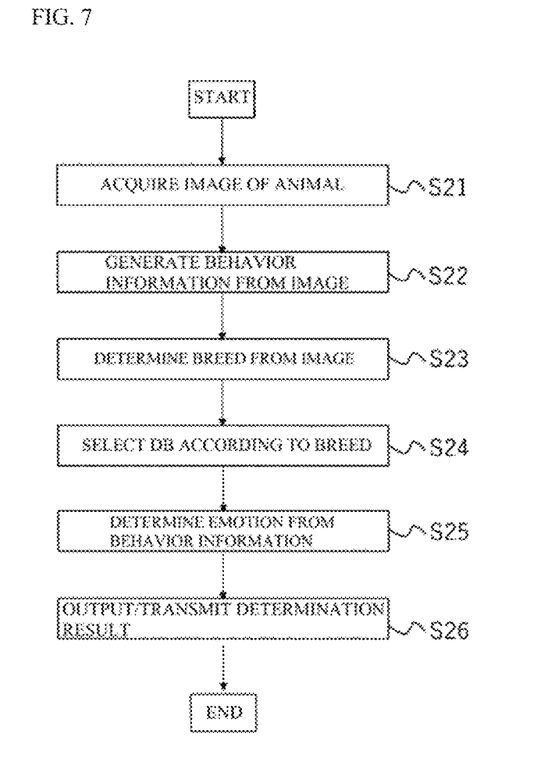
FIG. 7 is a flowchart diagram illustrating an example of the flow of emotion determination by the emotion determination system of the present invention (a case in which the breed is determined before the emotion is determined).

FIG. 7 illustrates a flowchart of emotion determination according to an embodiment in which the emotion determination system comprises the breed determination unit. A user inputs basic information such as the type of a target animal to the acquisition unit and uploads an image of the animal (step S21). The processing operation unit of the server uses the behavior information generation unit to determine the behavior of the animal from the uploaded image and generates behavior information (step S22). Next, the breed determination unit determines the breed from the image of the animal (step S23). Then, a database corresponding to the breed is selected (step S24), and by referring to the selected database, the emotion of the animal is determined from the behavior information (step S25). The output unit outputs and presents the derived determination result to the user by displaying it on a screen or by other means (step S26). Note that breed determination by the breed determination unit may be made before generation of the animal behavior information or simultaneously with the animal behavior information.

The image of an animal, learned model, behavior information generation, emotion determination, and the like are similar to those described with regard to the above emotion determination system of the present invention.

EXAMPLES

[Generation of a Learned Model for the Behavior Information Generation Unit]

As teacher data, 761 images of cats with raised tail (breakdown: images from behind, from the front, from the side, and sitting) and images of cats without raised tail (breakdown: images from behind, from the front, from the side, and sitting) were prepared respectively. The number of images per breakdown is as described in Table 1 below. These images were used as teacher data to train a neural network ResNet.

TABLE 1

| Breed/ behavior | Data classification | Behavior | Images from behind | Images from the front | Images from the side | Sitting images | Total |
|---|---|---|---|---|---|---|---|
| Cat/ raising tail | Learned count | Images with raised tail | 244 | 247 | 253 | 17 | 761 |
| | | Images without raised tail | 244 | 282 | 244 | 32 | 802 |
| | | Total | 488 | 529 | 497 | 49 | 1563 |

Next, the obtained learned model was evaluated. As described in Table 2 below, images with raised tail and images without raised tail were prepared as test images (images different from the teacher data). The number of correct answers in the test is also illustrated in Table 2.

TABLE 2

| Breed/ behavior | Data classification | Behavior | Images from behind | Images from the front | Images from the side | Sitting images | Total | Correct answer rate |
|---|---|---|---|---|---|---|---|---|
| Cat/ raising tail | Number of tests | Images with raised tail | 56 | 55 | 45 | 3 | 159 | — |
| | | Images without raised tail | 58 | 68 | 54 | 8 | 188 | — |
| | | Total | 114 | 123 | 99 | 11 | 347 | — |
| | Number of correct answers | Images with raised tail | 54 | 55 | 43 | 3 | 155 | 97% |
| | | Images without raised tail | 58 | 64 | 51 | 5 | 178 | 95% |
| | | Total | 112 | 119 | 94 | 8 | 333 | 96% |

As described above, a learned model capable of determining the behavior of a cat with high accuracy was generated from cat images.

[Creation of a Database on Correspondence Between Behavior and Emotion]

A database on correspondence between behavior information of cats and emotions was created as illustrated in Table 3 below by referring to the following documents. The term "bad condition" in Table 3 refers to a bad emotional condition, not a bad health condition, and is synonymous with "depressed."

Neko to kurashi daihyakka (https://test.anicom-sompo-.co.jp/nekonoshiori/)

Facial expressions of pain in cats: the development and validation of a Feline Grimace Scale (Sci Rep. 2019 Dec. 13; 9(1): 19128. doi: 10.1038/s41598-019-55693-8.)

The quality of being sociable: The influence of human attentional state, population, and human familiarity on domestic cat sociability (ehav Processes. 2019 January; 158:11-17. doi: 10.1016/j.beproc.2018.10.026. Epub 2018 Nov. 2.)

Attachment bonds between domestic cats and humans (CORRESPONDENCE|VOLUME 29, ISSUE 18, PR864-R865, Sep. 23, 2019)

Early weaning increases aggression and stereotypic behaviour in cats (Sci. Rep. volume 7, Article number: 10412 (2017))

The 'Feline Five': An exploration of personality in pet cats (*Felis catus*) (PLOS ONE Aug. 23, 2017)

Social interaction, food, scent or toys? A formal assessment of domestic pet and shelter cat (*Felis silvestris catus*) preferences (Behav Processes. 2017 August; 141 (Pt 3): 322-328. doi: 10.1016/j.beproc.2017.03.016.)

Social referencing and cat-human communication (Animal Cognition volume 18, pages 639-648 (2015))

Even healthy cats act sick when their routine is disrupted (https://www.sciencedaily.com/releases/2011/01/110103110357.htm)

TABLE 3

| Behavior information | | Happy | Relaxed | Seeking affection | Fun | Good mood | Alerted | Feared | Angry | Frustrated | Bad condition | Other |
|---|---|---|---|---|---|---|---|---|---|---|---|---|
| A0001 | Rounding pupils | | | | 0.5 | | 0.5 | | | | | |
| A0002 | Sharpening eyes | | | | | | | | 1 | | | |
| A0003 | Squinting | | 0.5 | | | | | | | | 0.5 | |
| A0004 | Pointing ears forward | | | | 1 | | | | | | | |
| A0005 | Pointing ears back | | | | | | 0.5 | 0.5 | | | | |
| A0006 | Opening mouth wide with fangs bared | | | | | | | | 1 | | | |
| A0007 | Pursing month | 0.5 | | | | 0.5 | | | | | | |
| A0008 | Flaccid whiskers | | 1 | | | | | | | | | |
| A0009 | Pointing whiskers upward | | | | 0.5 | | | | 0.5 | | | |
| A0010 | Positioning head below shoulders | | | | | | | | | | 1 | |
| A0011 | Rubbing head against something | | | 1 | | | | | | | | |
| A0012 | Bristling head fur | | | | | | | | 1 | | | |
| A0013 | Lying down with belly showing | | 1 | | | | | | | | | |
| A0014 | Rubbing body against owner | | | 1 | | | | | | | | |
| A0015 | Rubbing body against wall | 0.5 | | 0.5 | | | | | | | | |
| A0016 | Lowering front trunk and raising hindquarters | | | | 1 | | | | | | | |
| A0017 | Gripping the ground with claws out | | | | | | | | 1 | | | |
| A0018 | Tensing limbs and lifting back | | | | | | | | 1 | | | |
| A0019 | Raising tail | 0.5 | | 0.5 | | | | | | | | |
| A0020 | Bristling tail fur | | | | | | | | 1 | | | |
| A0021 | Curling tail | | | | | | 0.5 | 0.5 | | | | |
| A0022 | Slapping tail | | | | | | | | | 1 | | |
| A0023 | Slumping down tail | | | | | | 0.5 | | | | 0.5 | |
| A9999 | Other | | | | | | | | | | | 0 |

For each of the following Examples, a moving image of a cat was taken and the behavior was observed. The number of pixels was 12 megapixels and the frame rate was 5 FPS (0.2 seconds/frame).

Example 1

The breed of the cat was American Shorthair, and the shooting time was 13.4 seconds. When the moving image was input into a program for determining animal behavior stored in a computer (a learned model that has learned the relationship between images of cats and their behaviors by learning using images of cats and information on the types of behaviors as teacher data), the behavior information of "raising tail" was generated as described in Table 4 below. Since the duration was equal to the shooting time, the weight was set to 1.

TABLE 4

| | Behavior information | | Time duration (seconds) | Weight | Emotions | | | | | | | | | | |
|---|---|---|---|---|---|---|---|---|---|---|---|---|---|---|---|
| | | | | | Happy | Relaxed | Seeking affection | Fun | Good mood | Alerted | Feared | Angry | Frustrated | Bad condition | Other |
| Example 1 | Action 1 | Raising tail (A0019) | 13.4 | 1 | 0.5 | | 0.5 | | | | | | | | |
| | | | | | 0.5 | | 0.5 | | | | | | | | 0 |

Based on the above behavior information, the database described in Table 3 was referred to, and the cat in this moving image was determined to have emotions of 0.5 points for "happy" and 0.5 points for "seeking affection."

Example 2

The breed of the cat was mixed breed, and the shooting time was 9.8 seconds. When the moving image was input into a program for determining animal behavior stored in a computer, the behavior information of "raising tail" and "rubbing body against owner" was generated as described in Table 5 below. The durations were 6.4 seconds for "raising tail" and 3.4 seconds for "rubbing body against owner," so the weights were set to 0.65 and 0.35, respectively, based on the rates of duration.

TABLE 5

| | Behavior information | | Time duration (seconds) | Weight | Emotions | | | | | | | | | | |
|---|---|---|---|---|---|---|---|---|---|---|---|---|---|---|---|
| | | | | | Happy | Relaxed | Seeking affection | Fun | Good mood | Alerted | Feared | Angry | Frustrated | Bad condition | Other |
| Example 2 | Action 2 | Raising tail (A0019) | 6.4 | 0.65 | 0.5 | | 0.5 | | | | | | | | |
| | Action 3 | Rubbing body against owner (A0014) | 3.4 | 0.35 | | | 1 | | | | | | | | |
| | | | | | 0.327 | | 0.673 | | | | | | | | |

Based on the above behavior information, the database described in Table 3 was referred to, and the cat in this moving image was determined to have emotions of 0.5 points for "happy" and 0.5 points for "seeking affection" with regard to "raising tail" and 1 point for "seeking affection" with regard to "rubbing body against owner" respectively. As a result of adding the points by weighting, the emotion of the cat in this moving image was determined to be 0.327 points for "happy" and 0.673 points for "seeking affection."

Example 3

The breed of the cat was Scottish Fold, and the shooting time was 10 seconds. The moving image was input into a program for determining animal behavior stored in a computer, generating the behavior information of "raising tail" and "other" as described in Table 6 below. The durations were 7.0 seconds for "raising tail" and 3.0 seconds for "other," so the weights were set to 0.7 and 0.3, respectively, based on the rates of duration.

TABLE 6

| | Behavior information | | Time duration (seconds) | Weight | Emotions | | | | | | | | | | |
|---|---|---|---|---|---|---|---|---|---|---|---|---|---|---|---|
| | | | | | Happy | Relaxed | Seeking affection | Fun | Good mood | Alerted | Feared | Angry | Frustrated | Bad condition | Other |
| Example 3 | Action 4 | Raising tail (A0019) | 7.0 | 0.7 | 0.5 | | 0.5 | | | | | | | | |

TABLE 6-continued

| | Behavior information | Time duration (seconds) | Weight | Happy | Relaxed | Seeking affection | Fun | Good mood | Alerted | Feared | Angry | Frustrated | Bad condition | Other |
|---|---|---|---|---|---|---|---|---|---|---|---|---|---|---|
| Action 5 | Other (A9999) | 3.0 | 0.3 | | | | | | | | | | | 0 |
| | | | | 0.35 | | 0.35 | | | | | | | | 0 |

Based on the above behavior information, the database described in Table 3 was referred to and the cat in this moving image was determined to have emotions of 0.5 points for "happy" and 0.5 points for "seeking affection" with regard to "raising tail" and no specific emotion was assigned for "other." As a result of adding the points by weighting, the emotion of the cat in this moving image was determined to be 0.35 points for "happy" and 0.35 points for "seeking affection."

Example 4

The breed of the cat was mixed breed, and the shooting duration was 8.4 seconds. When the moving image was input into a program for determining animal behavior stored in a computer, the following behavior information of "pointing ears back," "opening mouth wide with fangs bared," "bristling head fur," and "bristling tail fur" was generated as described in Table 7 below. Since all of these behaviors were observed simultaneously and the duration was the same as the shooting time for any of the behaviors, the weight was ¼ each and set to 0.25 for all the four behaviors.

Based on the above behavior information, the database described in Table 3 was referred to, and the cat in this moving image was determined to have emotions of 0.5 points for "alerted" and 0.5 points for "angry" with regard to "pointing ears back," 1 point for "angry" with regard to "opening mouth wide with fangs bared," 1 point for "angry" with regard to "bristling head fur," and 1 point for "angry" with regard to "bristling tail fur." As a result of adding the points by weighting, the emotion of the cat in this moving image was determined to be 0.125 points for "alerted" and 0.875 points for "anger."

Example 5

The breed of the cat was Japanese cat (Wa-neko), and the shooting time was 16 seconds. When the moving image was input into a program for determining animal behavior stored in a computer, the behavior information of "squinting," "pursing mouth," and "lying down with belly showing," was generated as described in Table 8 below. Of these behaviors, "squinting" and "pursing mouth" were observed partially at the same time. The durations were 7.2 seconds for "squinting," 4.2 seconds for "pursing mouth," and 8.2 seconds for "lying down with belly showing," so the weights were set to 0.37, 0.21, and 0.42, respectively.

TABLE 7

| | | Behavior information | Time duration (seconds) | Weight | Happy | Relaxed | Seeking affection | Fun | Good mood | Alerted | Feared | Angry | Frustrated | Bad condition | Other |
|---|---|---|---|---|---|---|---|---|---|---|---|---|---|---|---|
| Example4 | Action 6-A | Pointing ears back (A0005) | 8.4 | 0.25 | | | | | | 0.5 | | 0.5 | | | |
| | Action 6-B | Opening mouth wide with fangs bared (A0006) | 8.4 | 0.25 | | | | | | | | 1 | | | |
| | Action 6-C | Bristling head fur (A0012) | 8.4 | 0.25 | | | | | | | | 1 | | | |
| | Action 6-D | Bristling tail fur (A0020) | 8.4 | 0.25 | | | | | | | | 1 | | | |
| | | | | | | | | | | 0.125 | | 0.875 | | | |

TABLE 8

| | Behavior information | Time duration (seconds) | Weight | Emotions | | | | | | | | | | |
|---|---|---|---|---|---|---|---|---|---|---|---|---|---|---|
| | | | | Happy | Relaxed | Seeking affection | Fun | Good mood | Alerted | Feared | Angry | Frustrated | Bad condition | Other |
| Example 5 — Action 7-A | Squinting (A0003) | 7.2 | 0.37 | | 0.5 | | | | | | | | 0.5 | |
| Action 7-B | Pursing mouth (A0007) | 4.2 | 0.21 | 0.5 | | | | 0.5 | | | | | | |
| Action 8 | Lying down with belly showing (A0013) | 8.2 | 0.42 | | 1 | | | | | | | | | |
| | | | | 0.107 | 0.602 | | | 0.107 | | | | | 0.184 | |

Based on the above behavior information, the database described in Table 3 was referred to, and the cat in the moving image was determined to have emotions of 0.5 points for "relaxed" and 0.5 points for "bad condition" with regard to "squinting," 0.5 points for "happy" and 0.5 points for "good mood" with regard to "pursing mouth," and 1 point for "relaxed" with regard to "lying down with belly showing." As a result of adding the points by weighting, the emotion of the cat in this moving image was determined to be 0.107 points for "happy," 0.602 points for "relaxed," 0.107 points for "good mood," and 0.184 points for "bad condition."

The invention claimed is:

1. An emotion determination system comprising:
   an acquisition unit for acquiring an image of an animal;
   a behavior information generation unit for generating behavior information relating to a behavior of the animal from the image of the animal acquired by the acquisition unit; and
   an emotion determination unit for determining an emotion of the animal based on the behavior information generated by the behavior information generation unit,
   wherein the image is a moving image, and the behavior information includes information relating to a duration of the behavior of the animal,
   wherein when the behavior information generation unit generates behavior information, and the behavior information is weighted according to a length of the duration of the behavior, and
   wherein each behavior information is assigned emotional points that have been set in advance, and the emotion determination unit determines emotion with a highest emotion point as a final emotion determination.

2. The emotion determination system according to claim 1, wherein the behavior information generation unit extracts a feature value from the image of the animal and generates behavior information by determining the behavior of the animal based on the feature value.

3. The emotion determination system according to claim 1, wherein the behavior information generation unit comprises a learned model that has learned a relationship between an image of an animal and a behavior of the animal, and generates behavior information by determining the behavior using the learned model.

4. The emotion determination system according to claim 1, wherein the behavior information generation unit generates behavior information for each behavior when a plurality of types of behaviors are included in the image.

5. The emotion determination system according to claim 1, further comprising a database storing correspondence between behavior information and an emotion,
   wherein the emotion determination unit determines an emotion of the animal by referring to the database.

6. The emotion determination system according to claim 1, further comprising a breed determination unit for determining a breed of the animal from the image of the animal acquired by the acquisition unit.

7. The emotion determination system according to claim 5, wherein the database is a database storing correspondence between behavior information and an emotion for each species or breed.

8. The emotion determination system according to claim 5, further comprising a plurality of the databases according to a classification that classifies a breed of an animal based on an average adult weight of the breed.

9. An emotion determination method comprising:
   a step of preparing an image of an animal;
   a behavior information generation step of generating behavior information relating to a behavior of the animal from the image of the animal by a computer; and
   an emotion determination step of determining an emotion of the animal based on the behavior information by a computer,
   wherein the image is a moving image, and the behavior information includes information relating to a duration of the behavior of the animal,
   wherein when the behavior information is generated in the behavior information generation step, and the behavior information is weighted according to a length of the duration of the behavior, and
   wherein each behavior information is assigned emotional points that have been set in advance, and the emotion determination step includes determining emotion with a highest emotion point as a final emotion determination.

10. The emotion determination method according to claim 9, wherein the behavior information generation step is a step of generating behavior information by extracting a feature value from the image of the animal and determining the behavior of the animal based on the feature value.

11. The emotion determination method according to claim 10, wherein the behavior information generation step is a step of generating behavior information by determining the behavior using a learned model that has learned a relationship between an image of an animal and a behavior of the animal.

12. The emotion determination system according to claim 2, wherein the behavior information generation unit generates behavior information for each behavior when a plurality of types of behaviors are included in the image.

13. The emotion determination system according to claim 3, wherein the behavior information generation unit generates behavior information for each behavior when a plurality of types of behaviors are included in the image.

14. The emotion determination system according to claim 2, further comprising a database storing correspondence between behavior information and an emotion,
 wherein the emotion determination unit determines an emotion of the animal by referring to the database.

15. The emotion determination system according to claim 3, further comprising a database storing correspondence between behavior information and an emotion,
 wherein the emotion determination unit determines an emotion of the animal by referring to the database.

16. The emotion determination system according to claim 4, further comprising a database storing correspondence between behavior information and an emotion,
 wherein the emotion determination unit determines an emotion of the animal by referring to the database.

17. The emotion determination system according to claim 1, wherein the emotion determination unit further determines emotions as follows:
 a) the emotional points assigned to the behavior information is multiplied by weighting of behavior information based on the duration of the behavior,
 b) the each emotional points obtained as a result of the multiplication are totaled, and
 c) emotions are determined according to the totaled emotional points.

18. The emotion determination system according to claim 1, wherein the moving image does not contain audio.

* * * * *